(12) United States Patent
Morioka

(10) Patent No.: US 8,512,686 B2
(45) Date of Patent: Aug. 20, 2013

(54) HAIR GROOMING PREPARATION

(75) Inventor: Tomoki Morioka, Tokyo (JP)

(73) Assignee: Kao Corporation, Tokyo (JP)

( * ) Notice: Subject to any disclaimer, the term of this patent is extended or adjusted under 35 U.S.C. 154(b) by 1108 days.

(21) Appl. No.: 10/566,498

(22) PCT Filed: Jul. 30, 2004

(86) PCT No.: PCT/JP2004/010961
§ 371 (c)(1), (2), (4) Date: Jan. 31, 2006

(87) PCT Pub. No.: WO2005/011623
PCT Pub. Date: Feb. 10, 2005

(65) Prior Publication Data
US 2006/0198807 A1 Sep. 7, 2006

(30) Foreign Application Priority Data

Aug. 1, 2003 (JP) ................. 2003-285444
Aug. 25, 2003 (JP) ................. 2003-299673

(51) Int. Cl.
*A61K 8/00* (2006.01)
(52) U.S. Cl.
USPC ....................... 424/70.19; 510/119
(58) Field of Classification Search
USPC ...................... 424/70.19; 510/119
See application file for complete search history.

(56) References Cited

U.S. PATENT DOCUMENTS

| | | | | |
|---|---|---|---|---|
| 5,785,962 A * | 7/1998 | Hinz et al. | ................. | 424/70.22 |
| 5,888,488 A * | 3/1999 | Fukuchi | ..................... | 424/70.12 |
| 6,923,954 B2 * | 8/2005 | Doi et al. | .................... | 424/70.19 |
| 2002/0037266 A1 | 3/2002 | Terazaki et al. | | |

FOREIGN PATENT DOCUMENTS

| | | |
|---|---|---|
| EP | 0 727 204 A1 | 8/1996 |
| EP | 0 858 794 A2 | 8/1998 |
| EP | 0 978 272 A1 | 2/2000 |
| EP | 1 174 112 A2 | 1/2002 |
| EP | 1 329 215 A2 | 7/2003 |
| EP | 1 537 847 A1 | 6/2005 |
| EP | 1 570 832 A1 | 9/2005 |
| GB | 2 321 595 A | 8/1998 |
| JP | 6-298625 | 10/1994 |
| JP | 8-239312 | 9/1996 |
| JP | 9-110650 | 4/1997 |
| JP | 10-218738 | 8/1998 |
| JP | 11-19945 | 7/1999 |
| JP | 11-199445 | 7/1999 |
| JP | 2000-109411 | 4/2000 |
| JP | 2001-192326 | 7/2001 |
| JP | 2001-220321 | 8/2001 |
| JP | 2002-29938 | 1/2002 |
| JP | 2002-29940 | 1/2002 |
| JP | 2002-47142 | 2/2002 |
| JP | 2002-338438 | 11/2002 |
| JP | 2003-212734 | 7/2003 |

OTHER PUBLICATIONS

Parchem, Cetyl Stearyl Alcohol, Material Safety Data Sheet, [online], Retrieved [Dec. 23, 2009], Retrieved from URL:< http://www.parchem.com/siteimages/Attachment/Cetyl%20Stearyl%20Alcohol%20MSDS.pdf>.*

Komori et al, Fragrance Journal, 2002, No. 6, p. 11-15 w/English abstract and Machine translation.

* cited by examiner

*Primary Examiner* — Lezah Roberts
*Assistant Examiner* — Nannette Holloman
(74) *Attorney, Agent, or Firm* — Oblon, Spivak, McClelland, Maier & Neustadt, L.L.P.

(57) ABSTRACT

Provided are a rinse-off, non-dyeing type hair cosmetic composition containing (a) a polycarboxylic acid or salt thereof, (b) a hydroxymonocarboxylic acid or salt thereof, and (c) an organic solvent selected from aromatic alcohols, alkylene carbonates and polyols at a weight ratio satisfying $0.33 \leq [(a)+(b)]/(c) \leq 2.5$, in which, the weight of each of (a) and (b) is that as an acid, and the composition has a pH at 25° C. of from 2.5 to 5 when diluted to 20 times the weight with water; and a method of treating hair, which contains using two hair cosmetic compositions A and B and treating the hair in the order of A→B or B→A; and a hair quality improving cosmetic set which contains the hair cosmetic compositions A and B:

A: Composition containing Components (a) and (c) at a weight ratio of (a)/(c)=0.6 or greater B: Composition containing Components (b) and (c) at a weight ratio of (b)/(c)=0.25 or greater.

The hair cosmetic composition and method of treating hair according to the invention have excellent effects for improving the elasticity and suppleness of the hair and give good feeling upon use during the treatment.

16 Claims, 1 Drawing Sheet

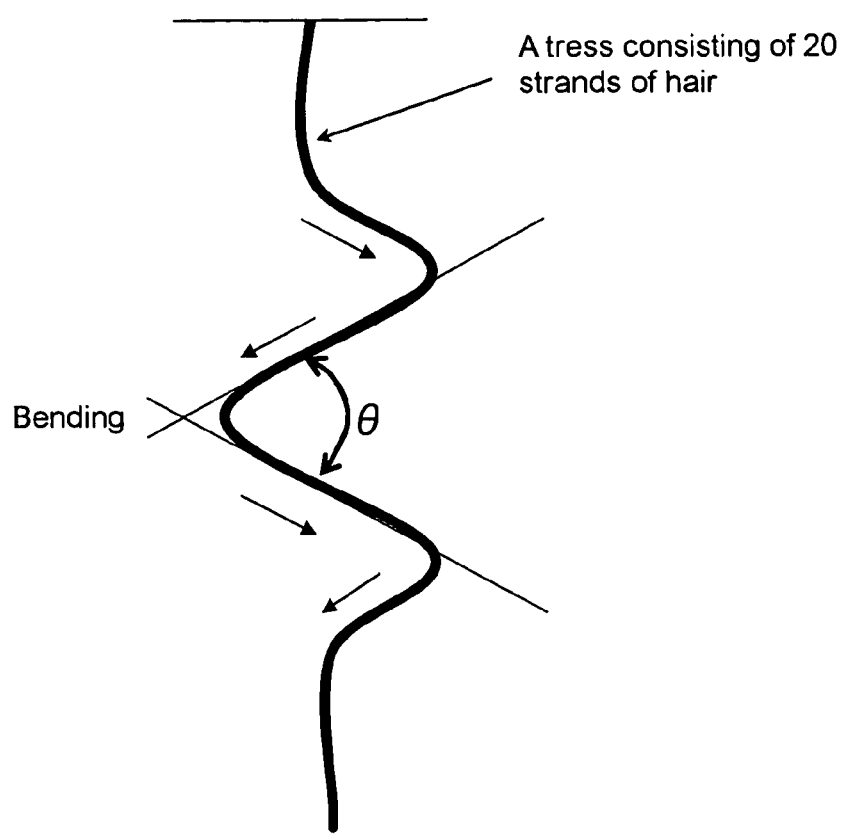

HAIR GROOMING PREPARATION

FIELD OF THE INVENTION

The present invention relates to a hair cosmetic composition having excellent effects for improving hair elasticity and suppleness and providing good feeling upon use; and method of treating hair with the composition.

BACKGROUND OF THE INVENTION

It is known that owing to the influence of chemical substances used for hair coloring or perming, or influence of heat upon hair blowing, hair system shrinks and many voids appear inside of the hair to cause drooping of the hair (e.g., refer to Non-patent document 1). Such damaged hair has poor elasticity, becomes excessively dry, cannot recover easily from a change in its shape such as a cow-lick or has poor manageability. At present, rinse-off hair cosmetic compositions contain an oil or fat, silicone, polymer or the like in order to prevent the hair from excessive drying, provide moist feel to the hair and improve hair smoothness. These compositions can provide temporal countermeasure by adhesion of such a component onto the hair, but cannot fundamentally improve the above-described troubles.

A hair cosmetic composition using an organic acid in combination with a specific organic solvent is known as those capable of improving hair quality, protecting the hair from excessive drying and providing the hair with manageability and luster (refer to Patent documents 1 and 2). The effects brought by a combination of only one kind of organic acid and the organic solvent, however, have not been satisfactory.
Non-patent document 1: Fragrance Journal, No. 6, p. 11(2000)
Patent document 1: JP-A-2002-47142
Patent document 2: JP-A-2002-29938

DISCLOSURE OF THE INVENTION

In a first aspect of the present invention, there is thus provided a rinse-off, non-dyeing type hair cosmetic composition containing the following components (a), (b) and (c):
(a) a polycarboxylic acid or salt thereof,
(b) a hydroxymonocarboxylic acid or salt thereof, and
(c) an organic solvent selected from aromatic alcohols, alkylene carbonates and polyols at a weight ratio satisfying $0.33 \leq [(a)+(b)]/(c) \leq 2.5$, in which the weight of each of (a) and (b) is that as an acid, and the composition has a pH from 2.5 to 5 at 25° C. when diluted to 20 times the weight with water.

In a second aspect of the present invention, there is also provided a method of treating hair, which contains using A: a hair cosmetic composition containing:
(a) a polycarboxylic acid or salt thereof, and
(c) an organic solvent selected from aromatic alcohols, alkylene carbonates and polyols at a weight ratio of (a)/(c)=0.6/1 or greater, and
B: another hair cosmetic composition containing:
(b) a hydroxymonocarboxylic acid or salt thereof, and
(c) an organic solvent selected from aromatic alcohols, alkylene carbonates and polyols at a weight ratio of (b)/(c)=0.25/1 or greater and treating hair with these cosmetic compositions in the order of A followed by B or vice versa; and provides a hair quality improving cosmetic set containing the above-described hair cosmetic compositions A and B.

BRIEF DESCRIPTION OF THE DRAWING

FIG. 1 illustrates a measuring method for the angle formed by flexion in the evaluation of the hair to which the hair cosmetic composition or method of treating hair of the present invention has been applied from the viewpoint of recovery from the signs which have remained after braiding.

DETAILED DESCRIPTION OF THE INVENTION

The present invention relates to a hair cosmetic composition and method of treating hair, each having excellent effects for improving the elasticity and suppleness of hair and providing good feeling upon use during treatment.

The present inventors have found that the above-described demand can be satisfied by using a polycarboxylic acid in combination with hydroxymonocarboxylic acid as an organic acid and using them with a specific organic solvent.

The polycarboxylic acid as Component (a) penetrates into the hair and gives the hair elasticity and also strength and body. Examples of the polycarboxylic acid include malonic acid, succinic acid, glutaric acid, adipic acid, maleic acid, fumaric acid, phthalic acid, oxalic acid, malic acid, tartaric acid and citric acid. Examples of the salt of the polycarboxylic acid include salts with an alkali metal, alkaline earth metal, ammonia and organic amine compound. Of these, malonic acid, maleic acid, and malic acid, and salts thereof are preferred, with malic acid and salts thereof being more preferred. These polycarboxylic acids may be used in combination of two or more of them.

In the first aspect (one-part composition), the content of Component (a) in the non-dyeing hair cosmetic composition of the invention is preferably from 0.05 to 10 wt. %, more preferably from 0.1 to 7.5 wt. %, even more preferably from 0.1 to 5 wt. % in view of the elasticity given to the hair and stability of the system.

In the second aspect (two-part cosmetic set), the content of Component (a) in the hair cosmetic composition A is preferably from 0.1 to 20 wt. %, more preferably from 0.2 to 15 wt. %, even more preferably from 0.2 to 10 wt. %.

The hydroxymonocarboxylic acid as Component (b) is to provide flexibility to hair by penetrating into the hair. Examples of the hydroxymonocarboxylic acid include glycolic acid and lactic acid, while examples of their salts include salts with an alkali metal, alkaline earth metal, ammonia and organic amine compound. These hydroxymonocarboxylic acids may be used in combination of two or more of them.

In the first aspect (one-part composition), the content of Component (b) in the non-dyeing hair cosmetic composition of the invention is preferably from 0.05 to 10 wt. %, more preferably from 0.1 to 7.5 wt. %, even more preferably from 0.1 to 5 wt. % in view of the flexibility given to the hair and stability of the system. Moreover, in the first aspect, a weight ratio of Component (a) to Component (b) (the weight of each of (a) and (b) is that as an acid) preferably ranges from 1:100 to 100:1, more preferably from 1:10 to 10:1 from the viewpoint of giving suppleness and manageability to the hair.

In the second aspect (two-part cosmetic set), the content of Component (b) in the hair cosmetic composition (B) is preferably from 0.1 to 20 wt. %, more preferably from 0.2 to 15 wt. %, even more preferably from 0.2 to 10 wt. %.

Examples of the aromatic alcohol as the organic solvent of Component (c) include benzyl alcohol, cinnamyl alcohol, phenethyl alcohol, p-anisyl alcohol, p-methylbenzyl alcohol, phenoxyethanol and 2-benzyloxyethanol. Examples of the alkylene carbonate include ethylene carbonate and propylene carbonate. Examples of the polyol include ethylene glycol, glycerin, sorbitol, propylene glycol, 1,3-butylene glycol, dipropylene glycol, and polypropylene glycol (preferably that having an average molecular weight (as measured by GPC) from 200 to 700, more preferably from 300 to 500). Examples of the preferred organic solvent as Component (c) include benzyl alcohol, benzyloxyethanol, propylene carbonate and polypropylene glycol (molecular weight: 400). These organic solvents may be used in combination of two or more of them.

In the first aspect (one-part composition), the content of the organic solvent in the non-dyeing hair cosmetic composition of the invention preferably ranges from 0.1 to 20 wt. %, more preferably from 0.5 to 10 wt. %, more preferably from 1 to 10 wt. % in view of promoting the penetration of the active ingredient and stability.

In the second aspect (two-part cosmetic set), the content of the organic solvent in each of the hair cosmetic compositions A and B preferably ranges from 0.1 to 20 wt. %, more preferably from 0.5 to 10 wt. %, even more preferably from 0.7 to 10 wt. %, still more preferably from 1 to 7 wt. %.

In the first aspect (one-part composition), the components (a), (b) and (c) are incorporated in the composition at a weight ratio satisfying $0.33 \leq [(a)+(b)]/(c) \leq 2.5$ (the weight of each of (a) and (b) is that as an acid) in consideration of the strength and body given to the hair and effective penetration of them into the hair. The weight ratio preferably falls within a range of from 0.35 to 2.3, especially preferably from 0.5 to 2.0.

In the second aspect (two-part cosmetic set), the components (a) and (c) are incorporated in the cosmetic composition A at a weight ratio (a)/(c) of 0.6 or greater, preferably from 0.6 to 5.0, more preferably from 0.6 to 1.5 in consideration of the strength and body given to hair and effective penetration of them into the hair. On the other hand, the components (b) and (c) are incorporated in the cosmetic composition B at a weight ratio (b)/(c) of 0.25 or greater, preferably from 0.25 to 10.0, more preferably from 0.25 to 1.0 from the viewpoint of flexibility and softness given to the hair and effective penetration of them into the hair.

The hair cosmetic composition of the invention can contain a surfactant as Component (d). Any one of cationic surfactant, anionic surfactant, nonionic surfactant and amphoteric surfactant may be used as the surfactant.

Examples of the cationic surfactant include quaternary ammonium salts represented by the following formula (1):

wherein, A represents a hydrogen atom or a linear or branched, saturated or unsaturated amide, N-hydrocarbon carbamoyl, acyloxy or hydrocarbonoxy group having 12 to 24 carbon atoms in total; B represents a linear or branched, saturated or unsaturated divalent $C_{1-22}$ hydrocarbon group; at least one of $R^1$, $R^2$ and $R^3$ represents a linear or branched alkyl or alkenyl group having 1 to 24 carbon atoms in total, while the remainder represents a $C_{1-3}$ alkyl group; and $X^-$ represents a halide ion or organic anion.

Examples of the quaternary ammonium salt represented by the formula (1) include mono(long chain alkyl) quaternary ammonium salts, di(long chain alkyl) quaternary ammonium salts, branched alkyl quaternary ammonium salts, alkylamidoalkylene quaternary ammonium salts, N-(hydrocarbon carbamoyl) alkylene quaternary ammonium salts, acyloxyalkylene quaternary ammonium salts and hydrocarbonoxy alkylene quaternary ammonium salts.

The mono(long chain alkyl) quaternary ammonium salts include stearyltrimethylammonium chloride, cetyltrimethylammonium chloride, behenyltrimethylammonium chloride and lauryltrimethylammonium chloride. The alkylamidoalkylene quaternary ammonium salts include stearamidopropyl quaternary ammonium salt. The N-(hydrocarbon carbamoyl)alkylene quaternary ammonium salts include N-stearylcarbamoylpropyl quaternary ammonium salt. The acyloxyalkylene quaternary ammonium salts include stearoxypropyl quaternary ammonium salt. The hydrocarbon oxyalkylene quaternary ammonium salts include octadecyloxypropyltrimethylammonium chloride.

As the other cationic surfactant, tertiary amine compounds represented by the following formula (2):

wherein, A and B have the same meanings as described above and $Y^1$ and $Y^2$ each independently represents a $C_{1-4}$ alkyl group, or salts thereof can be used.

In the tertiary amine compound (2), when A represents a group other than a hydrogen atom, A preferably represents an amide group or a hydrocarbonoxy group having 14 to 22, preferably 18 to 22 carbon atoms in total. Moreover, its hydrocarbon moiety is preferably a saturated one, more preferably a linear saturated one. In this case, B preferably represents a trimethylene group. When A represents a hydrogen atom, on the other hand, B preferably represents a $C_{18-22}$ group, with a saturated group, preferably a saturated linear group being preferred. Examples of $Y^1$ and $Y^2$ include methyl, ethyl, propyl, isopropyl, butyl and tert-butyl groups, of which methyl and ethyl groups are preferred, with methyl group being more preferred. Specific preferred examples of the tertiary amine compound (2) include N,N-dimethyloctadecyloxypropylamine and stearamidopropyldimethylamine.

The salt of the tertiary amine compound (2) is formed by the neutralization between the above-described tertiary amine compound and the organic acid, acidic amino acid or inorganic acid as Component (a) or (b).

Examples of the anionic surfactant include sulfates, sulfonates and carboxylates, specifically, polyoxyethylene alkyl ether sulfates, polyoxyethylene alkenyl ether sulfates, alkyl sulfates, polyoxyalkylene alkyl phenyl ether sulfates, alkyl sulfosuccinates, polyoxyalkylene alkyl sulfosuccinates, alkanesulfonates, and higher fatty acid salts. Those represented by the following formula (3) or (4) are preferred.

wherein, $R^4$ represents a $C_{10-18}$ alkyl or alkenyl group, $R^5$ represents a $C_{10-18}$ alkyl group, M represents an alkali metal, alkaline earth metal, ammonium, alkanolamine or basic amino acid, and m stands for a number from 1 to 5, which is a weight average.

In the formula (3), m is preferably from 0.6 to 1.4 from the viewpoints of foaming property and smoothness.

Examples of the nonionic surfactant include polyoxyalkylene sorbitan fatty acid esters, polyoxyalkylene sorbitol fatty acid esters, polyoxyalkylene glycerin fatty acid esters, polyoxyalkylene fatty acid esters, polyoxyalkylene alkyl ethers, polyoxyalkylene alkylphenyl ethers, polyoxyalkylene (hydrogenated) castor oils, sucrose fatty acid esters, polyglycerin alkyl ethers, polyglycerin fatty acid esters, fatty acid alkanolamides and alkyl glycosides. Of these, alkyl glycosides, polyoxyalkylene $C_{8-20}$ fatty acid esters, polyoxyethylene sorbitan fatty acid esters, polyoxyethylene hydrogenated castor oils and fatty acid alkanolamides are preferred. As the fatty acid alkanolamides, those having a $C_{8-18}$, preferably $C_{10-16}$ acyl group are preferred. They may be either monoalkanolamides or dialkanolamides, of which those having a $C_{2-3}$ hydroxyalkyl group are preferred. Examples include oleic diethanolamide, palm kernel fatty acid diethanolamide, coconut fatty acid diethanolamide, lauric diethanolamide, polyoxyethylene coconut fatty acid monoethanolamide, coconut fatty acid monoethanolamide, lauric isopropanolamide and lauric monoethanolamide.

As the amphoteric surfactant, betaine surfactants can be used. Of these, alkyldimethylaminoacetic acid betaines and fatty acid amidopropylbetaines are more preferred, with fatty acid amidopropylbetaines being preferred. As the fatty acid amidopropylbetaines, those having a $C_{8-18}$, especially $C_{10-16}$ acyl group are preferred. Preferred examples of the fatty acid amidopropylbetaines are lauric amidopropylbetaine, palm kernel fatty acid amidopropylbetaines and coconut fatty acid amidopropylbetaines.

The above-described surfactants may be used in combination of two or more of them. Their preferred contents will next be described.

In the first aspect (one-part composition), the content of the cationic surfactant in the non-dyeing hair cosmetic composition of the invention is preferably from 0.1 to 20 wt. %, more preferably from 0.5 to 15 wt. %, more preferably from 0.5 to 10 wt. % in view of the conditioning effects and stability. The content of the anionic surfactant in the non-dying hair cosmetic composition of the invention is preferably from 1 to 50 wt. %, more preferably from 5 to 30 wt. %, even more preferably from 8 to 22 wt. %, in view of the stability of the non-dyeing hair cosmetic composition, liquid property upon use, and easy lathering as well as washing upon shampooing. The content of each of the nonionic surfactant and amphoteric surfactant in the non-dyeing hair cosmetic composition of the invention is preferably from 0.1 to 30 wt. %, more preferably from 0.2 to 20 wt. %, even more preferably from 0.5 to 10 wt. % in view of stability and liquid property upon use.

In the case of the second aspect (two-part cosmetic set), the content of the cationic surfactant in the hair cosmetic composition of the invention is preferably from 0.1 to 20 wt. %, more preferably from 0.5 to 15 wt. %, even more preferably from 0.5 to 10 wt. % from the viewpoints of its conditioning effects. The sum total content of all the surfactants in a hair shampoo is preferably from 0.1 to 50 wt. %, more preferably from 1 to 30 wt. %, still more preferably from 5 to 25 wt. %, still more preferably from 5 to 20 wt. %, while that in a hair rinse, hair conditioner, hair treatment or the like is preferably from 0.1 to 20 wt. %, more preferably from 0.5 to 10 wt. %, even more preferably from 1 to 5 wt. %.

The hair cosmetic composition of the invention may contain a higher alcohol. As the higher alcohol, those having a $C_{12-28}$ alkyl group are preferred, with those having a $C_{16-24}$, preferably $C_{22}$ alkyl group being preferred. This alkyl group is preferably a linear one. Examples of the higher alcohol include cetyl alcohol, stearyl alcohol, aralkyl alcohol and behenyl alcohol. Of these, behenyl alcohol is preferred.

The higher alcohols may be used in combination of two or more of them. Its (or their) content in the hair cosmetic composition of the invention is preferably from 1 to 20 wt. %, more preferably from 1 to 10 wt. %, even more preferably from 2 to 8 wt. %, in each of the first aspect and second aspect.

With a view toward improving the feeling during rinsing with water and improving the feeling on finish after hair drying, the hair cosmetic composition of the invention may further contain a silicone such as dimethylpolysiloxane, cyclic dimethylpolysiloxane, amino-modified polysiloxane, alkyl-modified polysiloxane, fluorine-modified polysiloxane, polyoxyalkylene-modified polysiloxane, carboxylic-acid-modified polysiloxane, alcohol-modified polysiloxane and epoxy-modified polysiloxane.

These silicones may be used in combination of two or more of them. Its (or their) content in the hair cosmetic composition of the invention is preferably from 0.1 to 20 wt. %, more preferably from 0.5 to 10 wt. %, in each of the first and second aspects.

With a view toward improving the feeling after drying (i.e., nongreasy feel, moist feel, etc.), the hair cosmetic composition may contain an oil component. Examples of the oil component include liquid fats and oils such as linseed oil, camellia oil, macadamia nut oil, corn oil, mink oil, olive oil, avocado oil, sasanqua oil, castor oil, safflower oil, jojoba oil, sunflower oil, almond oil, rapeseed oil, sesame oil, soybean oil, peanut oil, meadow foam oil, triglycerin, glycerin trioctanoate, and glycerin triisopalmitate; ester oils such as cetyl octanoate, hexyl laurate, isopropyl myristate, myristyl myristate, isopropyl palmitate, octyl palmitate, hexadecyl palmitate, isocetyl stearate, hydrogenated castor oil stearate, hydrogenated castor oil monohydroxystearate, isopropyl isostearate, octyl isopalmitate, isodecyl oleate, glyceryl tri-2-ethylhexanoate, pentaerythritol tetra-2-ethylhexanoate, 2-ethylhexyl succinate and diethyl sabacate; hydrocarbons such as liquid paraffin, squalane, squalene, paraffin, isoparaffin and ceresin; and fatty acids such as lauric acid, myristic acid, palmitic acid, oleic acid and stearic acid. Two or more of these oils may be used in combination. The content of each oil component in the hair cosmetic composition of the invention is preferably from 0.01 to 20 wt. %, more preferably from 0.1 to 10 wt. %.

The hair cosmetic composition of the invention may contain other component according to the objectives. Examples include sequestering agents such as sodium EDTA and sodium metaphosphate; neutralizing agents such as 2-amino-2-methyl-1-propanol, potassium hydroxide, sodium hydroxide, triethanolamine and sodium carbonate; antioxidants such as ascorbic acid, α-tocopherol, and dibutylhydroxyanisole; and others such as water soluble polymer, film forming resin, medicinal component, antibiotic, antidandruff, UV absorber, perfume and colorant.

The non-dyeing hair cosmetic composition according to the first aspect (one-part composition) can be prepared by mixing Components (a), (b) and (c), the above-described other component as needed depending on the objectives, and water. The non-dyeing hair cosmetic composition of the invention preferably has a pH at 25° C. of from 2.5 to 5, more preferably from 3 to 3.9 when diluted to 20 times the weight with water.

The hair cosmetic compositions A and B according to the second aspect (two-part cosmetic set) can be prepared by mixing Components (a) and (c), or (b) and (c), plus the above-described other component as needed depending on the objectives, and water. The hair cosmetic compositions A and B each preferably has a pH at 25° C. of from 2 to 5.5, more preferably from 2.5 to 5, even more preferably from 3 to 3.9 when diluted to 20 times the weight with water.

The form of non-dyeing hair cosmetic composition according to the first aspect (one-part composition) is not limited insofar as it is a rinse-off type. Examples include hair shampoo, hair rinse, hair conditioner and hair treatment.

Concerning the hair cosmetic compositions A and B in the second aspect (two-part cosmetic set), both may be a rinse-off type as described above or both may be a leave-on type (such as hair styling agent and leave-on treatment). Alternatively, the hair cosmetic composition to be applied first may be a rinse-off type and that to be applied next may be a leave-on type. As the typical examples of the second aspect, following combinations can be given.

(1) Combination of Rinse-Off Type Hair Cosmetic Compositions
   Hair shampoo and hair shampoo
   Hair shampoo and hair rinse (embracing hair conditioner and hair treatment. This will equally apply hereinafter)
   Hair rinse and hair rinse
(2) Combination of Leave-On Type Hair Cosmetic Compositions
   Leave-on treatment and hair styling agent
   Leave-on treatment and leave-on treatment
(3) Combination of a Rinse-Off Type Hair Cosmetic Composition and a Leave-On Type Hair Cosmetic Composition
   Hair shampoo and leave-on treatment
   Hair rinse and hair styling agent Of these combinations, that of rinse-off hair cosmetic compositions (1), especially that of a hair shampoo and a hair rinse is preferred.

In the second aspect, the hair may be treated successively with (a) the hair cosmetic composition A containing a polycarboxylic acid or salt thereof and (b) the hair cosmetic composition B containing (b) a hydroxymonocarboxylic acid or salt thereof. The compositions (A) and (B) can be used in any order, but treatment first with the hair cosmetic composition A followed by the treatment with the hair cosmetic composition B is preferred because it brings about higher effects. The organic acid incorporated in a hair shampoo is preferably a polycarboxylic acid in view of feeling upon use, while that incorporated in a hair rinse is preferably a hydroxymonocarboxylic acid in view of feeling upon use. For the combination of a hair shampoo and a hair rinse, use of the hair cosmetic composition A for the hair shampoo and the hair cosmetic composition B for the hair rinse is preferred.

EXAMPLES

Examples 1 to 4, and Comparative Examples 1 to 4

Hair shampoos as shown in Table 1 were prepared. The hair shampooed with each of them was evaluated for resistance of hair against remaining of signs after braiding and recovery from the signs as indices of the elasticity and suppleness of the hair. The results are shown collectively in Table 1.

[Resistance of Hair Against Remaining of Signs After Braiding and Recovery from the Signs]

To a hair tress (consisting of 20 strands of hair) damaged by bleaching, 1 g of a hair shampoo was applied. After it was allowed to stand at 35° C. for 15 minutes, it was rinsed and blow dried well (this treatment corresponded to an instance of continuous use of the hair shampoo for 1 week). This hair treatment was repeated 4 times.

The hair treated in the above-described manner was evaluated for its resistance against remaining of signs after braiding and recovery from the signs using a fixing tool having, at an interval of 18 mm, two φ 4-mm metal made supports. The hair tress was wound around these two metal supports in the shape of a cross under a load of 80 g. After the hair tress was fixed under the conditions of 20° C. and 20% humidity for 1 hour, the angle of the sign formed by bending, as illustrated in FIG. 1, when the hair tress was released from these two metal supports was measured.

The angle of the sign formed by bending was measured just after release and one hour after release. In accordance with the below-described equation, recovery (%) was calculated based on the angle (θ) of the sign formed by bending.

Recovery (%) from sign formed by bending = sin(θ/2)×100

TABLE 1

| Raw material | Ex. 1 | Comp. Ex. 1 | Ex. 2 | Comp. Ex. 2 | Ex. 3 | Comp. Ex. 3 | Ex. 4 | Comp. Ex. 4a | (wt. %) Comp. Ex. 4b |
|---|---|---|---|---|---|---|---|---|---|
| Sodium polyoxyethylene lauryl ether sulfate | 10.00 | 10.00 | 12.00 | 12.00 | 10.00 | 10.00 | 10.00 | 10.00 | 10.00 |
| Sodium lauryl sulfate | 4.00 | 4.00 | — | — | 5.00 | 5.00 | 5.00 | 5.00 | 5.00 |
| Lauric amidopropylbetaine | 3.00 | 3.00 | 3.00 | 3.00 | — | — | 2.50 | 2.50 | 2.50 |
| Polyoxyethylene lauryl ether (16 E.O.) | 2.00 | 2.00 | 2.00 | 2.00 | — | — | 2.00 | 2.00 | 2.00 |
| Coconut fatty acid monoethanolamide | 0.80 | 0.80 | 0.40 | 0.40 | — | — | 0.50 | 0.50 | 0.50 |
| Myristyl alcohol | 1.00 | 1.00 | 1.00 | 1.00 | 1.00 | 1.00 | 1.00 | 1.00 | 1.00 |
| Highly polymerized Methylpolysiloxane emulsion | 4.00 | 4.00 | — | — | 1.60 | 1.60 | — | — | — |
| Pearl concentrate | 8.00 | 8.00 | 8.00 | 8.00 | 12.00 | 12.00 | 8.00 | 8.00 | 8.00 |
| (c): PPG400 | 1.00 | — | 1.00 | — | 0.10 | 0.10 | 1.00 | 1.00 | 1.00 |
| (c): Benzyl alcohol | — | — | — | — | 0.50 | 0.50 | — | — | — |
| (c): Benzyloxyethanol | — | — | — | — | — | — | 0.50 | 0.50 | 0.50 |
| (c): Phenoxyethanol | — | — | 0.40 | — | — | — | — | — | — |
| Phosphoric acid | — | q.s. | — | — | — | q.s. | — | q.s. | q.s. |
| (b): Lactic acid | 1.00 | — | — | — | 0.75 | — | 0.30 | — | 0.30 |
| (b): Glycolic acid | — | — | 0.70 | 0.70 | — | — | 0.50 | — | 0.50 |
| (a): Citric acid | — | — | — | — | — | — | 0.20 | 0.20 | — |
| (a): Malic acid | 0.80 | — | 1.00 | 1.00 | 0.75 | — | 0.80 | 0.80 | — |
| Cationic cellulose | 0.50 | 0.50 | 0.40 | 0.40 | 0.30 | 0.30 | 0.50 | 0.50 | 0.50 |
| Cationic guar gum | — | — | 0.20 | 0.20 | 0.40 | 0.40 | — | — | — |
| Dimethyldialkylammonium chloride/acrylamide copolymer | 0.10 | 0.10 | — | — | — | — | 0.10 | 0.10 | 0.10 |

TABLE 1-continued

| Raw material | | Ex. 1 | Comp. Ex. 1 | Ex. 2 | Comp. Ex. 2 | Ex. 3 | Comp. Ex. 3 | Ex. 4 | Comp. Ex. 4a | (wt. %) Comp. Ex. 4b |
|---|---|---|---|---|---|---|---|---|---|---|
| Sodium chloride | | 0.20 | 0.20 | 0.25 | 0.25 | 0.20 | 0.20 | 0.20 | 0.20 | 0.20 |
| Sodium hydroxide | | q.s. | q.s. | q.s. | q.s. | q.s. | q.s. | q.s. | q.s. | q.s. |
| Perfume | | 0.50 | 0.50 | 0.40 | 0.40 | 0.60 | 0.60 | 0.50 | 0.50 | 0.50 |
| Purified water | | balance | balance | balance | balance | balance | balance | balance | balance | balance |
| pH (diluted to 20 times the weight with water, 25° C.) | | 3.7 | 5.5 | 3.7 | 3.7 | 3.7 | 5.5 | 3.7 | 3.7 | 3.7 |
| [(a) + (b)]/(c) | | 1.8 | — | 1.21 | ∞ | 2.5 | 0 | 1.2 | 0.67 | 0.53 |
| Recovery (%) from signs formed by Bending | Just after | 80 | 54 | 82 | 70 | 80 | 55 | 79 | 68 | 62 |
| | One hour after | 96 | 81 | 97 | 90 | 97 | 84 | 97 | 90 | 88 |

Examples 5 to 8 and Comparative Examples 5 to 8

The hair conditioners shown in Table 2 were prepared and the hair treated therewith in accordance with the below-described method was evaluated for resistance of hair against remaining of signs after braiding and recovery from the signs in a manner similar to the above-described one. The results are shown collectively in Table 2.

(Treating Method)

A hair tress (consisting of 20 strands of hair) damaged by bleaching was washed with 1 g of a plain shampoo. To the resulting hair, 1 g of the hair conditioner was applied. It was allowed to stand at 35° C. for 15 minutes, then rinsed, and blow dried sufficiently (this treatment corresponds to an instance of continuous use of a hair shampoo and hair conditioner for 1 week). The above treatment was repeated 4 times.

Examples 9 to 12, and Comparative Examples 9 to 15

The hair shampoos shown in Table 3 and hair conditioners shown in Table 4 were prepared.

[Resistance of Hair Against Remaining of Signs After Braiding and Recovery from the Signs]

The hair treated in the below-described method was evaluated for its resistance against remaining of signs formed by braiding and recovery from the signs in the above-described manner. The results are shown collectively in Table 5.

(Treating Method)

To a hair tress (consisting of 20 strands of hair) damaged by bleaching, 1 g of a plain shampoo was applied. It was allowed to stand at 35° C. for 15 minutes. Then, 1 g of the hair conditioner was applied to the resulting hair. It was allowed to stand at 35° C. for 15 minutes, then rinsed, and blow dried

TABLE 2

| Raw material | | Ex. 5 | Comp. Ex. 5 | Ex. 6 | Comp. Ex. 6 | Ex. 7 | Comp. Ex. 7 | Ex. 8 | Comp. Ex. 8a | (wt. %) Comp. Ex. 8b |
|---|---|---|---|---|---|---|---|---|---|---|
| Behenyltrimethylammonium chloride | | — | — | 6.00 | 6.00 | 2.90 | 2.90 | — | — | — |
| Dimethyloctadecyloxypropylamine | | 2.00 | 2.00 | — | — | — | — | 3.00 | 3.00 | 3.00 |
| Stearyl alcohol | | 6.00 | 6.00 | — | — | — | — | 9.00 | 9.00 | 9.00 |
| Behenyl alcohol | | — | — | 14.00 | 14.00 | 5.00 | 5.00 | — | — | — |
| Dipentaerythritol fatty acid ester | | — | — | 0.10 | 0.10 | 0.20 | 0.20 | 0.20 | 0.20 | 0.20 |
| Isopropyl palmitate | | — | — | 1.00 | 1.00 | 0.50 | 0.50 | — | — | — |
| Paraffin wax | | 0.50 | 0.50 | — | — | — | — | 0.50 | 0.50 | 0.50 |
| Methylpolysiloxane | | 3.50 | 3.50 | 4.00 | 4.00 | 2.70 | 2.70 | 5.00 | 5.00 | 5.00 |
| Amino-modified silicone | | 0.50 | 0.50 | 0.50 | 0.50 | — | — | 2.50 | 2.50 | 2.50 |
| (c): PPG400 | | — | — | 5.00 | — | 2.50 | 2.50 | — | — | — |
| (c): Benzyloxyethanol | | 1.00 | — | 1.00 | — | — | — | 1.50 | 1.50 | 1.50 |
| (c): Dipropylene glycol | | 5.00 | — | — | — | 5.00 | 5.00 | 2.50 | 2.50 | 2.50 |
| (c): Phenoxyethanol | | 0.10 | — | 0.10 | — | 0.10 | 0.10 | 0.10 | 0.10 | 0.10 |
| Phosphoric acid | | — | q.s. | — | — | — | q.s. | — | q.s. | q.s. |
| (b): Lactic acid | | 2.30 | — | 1.00 | 1.00 | 2.00 | — | 1.80 | 1.80 | — |
| (b): Glycolic acid | | — | — | 1.20 | 1.20 | — | — | — | — | — |
| (a): Malic acid | | 0.80 | — | 0.80 | 0.70 | 0.80 | — | 1.00 | — | 1.00 |
| Hydroxyethyl cellulose | | 0.30 | 0.30 | 0.20 | 0.20 | — | — | 0.30 | 0.30 | 0.30 |
| Highly polymerized polyethylene glycol | | — | — | 0.08 | 0.08 | 0.08 | 0.08 | — | — | — |
| 48 wt. % sodium hydroxide | | q.s. | q.s. | q.s. | q.s. | q.s. | q.s. | q.s. | q.s. | q.s. |
| Perfume | | 0.40 | 0.40 | 0.20 | 0.20 | 0.40 | 0.40 | 0.35 | 0.35 | 0.35 |
| Purified water | | balance | balance | balance | balance | balance | balance | balance | balance | balance |
| pH (diluted to 20 times the weight with water, 25° C.) | | 3.0 | 5.0 | 3.0 | 3.0 | 3.0 | 5.0 | 3.0 | 3.0 | 3.0 |
| [(a) + (b)]/(c) | | 0.5 | — | 0.49 | ∞ | 0.37 | 0 | 0.68 | 0.43 | 0.24 |
| Recovery (%) from signs formed by bending | Rightly after | 79 | 56 | 82 | 68 | 80 | 57 | 79 | 60 | 66 |
| | One hour after | 96 | 83 | 97 | 90 | 97 | 85 | 97 | 88 | 91 | sufficiently (this treatment corresponds to an instance of continuous use of a hair shampoo and a hair conditioner for 1 week). The above treatment was repeated 4 times.

[Feeling Upon Use]

A tress of about 30 g in weight and 25 cm in length was shampooed with 3 g of a hair shampoo. After rough removal of water from the hair, 3 g of a hair conditioner was applied, followed by rinsing with running water. The smoothness during the time from application to rinsing was organoleptically evaluated under the following criteria. The results are shown in Table 5.

A: The agents spread well and have excellent smoothness and their effects last very long.
B: They have good smoothness and their effects last long.
C: They do not have good smoothness.
D: They do not spread well with some friction or disturbance.

TABLE 3

| Hair shampoo | Ex. 9 | Comp. Ex. 9 | Ex. 10 | Comp. Ex. 10 | Ex. 11 | Comp. Ex. 11 | Ex. 12 | Comp. Ex. 12 | Comp. Ex. 13 | Comp. Ex. 14 | Comp. Ex. 15 (wt. %) |
|---|---|---|---|---|---|---|---|---|---|---|---|
| Sodium polyoxyethylene lauryl ether sulfate | 10.00 | 10.00 | 12.00 | 12.00 | 10.00 | 10.00 | 10.00 | 10.00 | 10.00 | 10.00 | 10.00 |
| Sodium lauryl sulfate | 4.00 | 4.00 | — | — | 5.00 | 5.00 | 5.00 | 5.00 | 5.00 | 5.00 | 5.00 |
| Lauric amidopropylbetaine | 3.00 | 3.00 | 3.00 | 3.00 | — | — | 2.50 | 2.50 | 2.50 | 2.50 | 2.50 |
| Polyoxyethylene lauryl ether (16E.O.) | 2.00 | 2.00 | 2.00 | 2.00 | — | — | 2.00 | 2.00 | 2.00 | 2.00 | 2.00 |
| Coconut fatty acid monoethanolamide | 0.80 | 0.80 | 0.40 | 0.40 | — | — | 0.50 | 0.50 | 0.50 | 0.50 | 0.50 |
| Myristyl alcohol | 1.00 | 1.00 | 1.00 | 1.00 | 1.00 | 1.00 | 1.00 | 1.00 | 1.00 | 1.00 | 1.00 |
| Highly polymerized methylpolysiloxane emulsion | 4.00 | 4.00 | — | — | 1.60 | 1.60 | — | — | — | — | — |
| Pearl concentrate | 8.00 | 8.00 | 8.00 | 8.00 | 12.00 | 12.00 | 8.00 | 8.00 | 8.00 | 8.00 | 8.00 |
| (b): PPG400 | 1.00 | — | 1.00 | — | 0.10 | 0.10 | 1.00 | 1.00 | 1.00 | 1.00 | 2.00 |
| (b): Benzyl alcohol | — | — | — | — | 0.50 | 0.50 | — | — | — | — | — |
| (b): Benzyloxyethanol | — | — | — | — | — | — | 0.50 | 0.50 | 0.50 | 0.50 | 1.00 |
| (b): Phenoxyethanol | — | — | 0.40 | — | — | — | — | — | — | — | — |
| Phosphoric acid | q.s. | q.s. | q.s. | q.s. | q.s. | q.s. | q.s. | q.s. | q.s. | q.s. | q.s. |
| (a2): Lactic acid | — | — | — | — | — | — | — | — | 1.00 | — | — |
| (a1): Malic acid | 0.80 | — | 1.00 | — | 0.75 | 0.75 | 1.00 | 1.00 | — | 0.70 | 0.70 |
| Cationic cellulose | 0.50 | 0.50 | 0.40 | 0.40 | 0.30 | 0.30 | 0.50 | 0.50 | 0.50 | 0.50 | 0.50 |
| Cationic guar gum | — | — | 0.20 | 0.20 | 0.40 | 0.40 | — | — | — | — | — |
| Dimethyldialkylammonium chloride/acrylamide copolymer | 0.10 | 0.10 | — | — | — | — | 0.10 | 0.10 | 0.10 | 0.10 | 0.10 |
| Sodium chloride | 0.20 | 0.20 | 0.25 | 0.25 | 0.20 | 0.20 | 0.20 | 0.20 | 0.20 | 0.20 | 0.20 |
| Perfume | 0.50 | 0.50 | 0.40 | 0.40 | 0.60 | 0.60 | 0.50 | 0.50 | 0.50 | 0.50 | 0.50 |
| Purified water | balance | balance | balance | balance | balance | balance | balance | balance | balance | balance | balance |
| pH (diluted to 20 times the weight With water, 25° C.) | 3.7 | 5.0 | 3.7 | 5.0 | 3.7 | 3.7 | 3.7 | 3.7 | 3.7 | 3.7 | 3.7 |

TABLE 4

| Hair conditioner | Ex. 9 | Comp Ex 9 | Ex. 10 | Comp Ex 10 | Ex. 11 | Comp Ex 11 | Ex. 12 | Comp Ex 12 | Comp Ex 13 | Comp Ex 14 | Comp Ex 15 (wt. %) |
|---|---|---|---|---|---|---|---|---|---|---|---|
| Behenyltrimethylammonium chloride | — | — | 6.00 | 6.00 | 2.90 | 2.90 | — | — | — | — | — |
| Dimethyloctadecyloxypropylamine | 2.00 | 2.00 | — | — | — | — | 3.00 | 3.00 | 3.00 | 3.00 | 3.00 |
| Stearyl alcohol | 6.00 | 6.00 | — | — | — | — | 9.00 | 9.00 | 9.00 | 9.00 | 9.00 |
| Behenyl alcohol | — | — | 14.00 | 14.00 | 5.00 | 5.00 | — | — | — | — | — |
| Dipentaerythritol fatty acid ester | — | — | 0.10 | 0.10 | 0.20 | 0.20 | 0.20 | 0.20 | 0.20 | 0.20 | 0.20 |
| Isopropyl palmitate | — | — | 1.00 | 1.00 | 0.50 | 0.50 | — | — | — | — | — |
| Paraffin wax | 0.50 | 0.50 | — | — | — | — | 0.50 | 0.50 | 0.50 | 0.50 | 0.50 |
| Methylpolysiloxane | 3.50 | 3.50 | 4.00 | 4.00 | 2.70 | 2.70 | 5.00 | 5.00 | 5.00 | 5.00 | 5.00 |
| Amino-modified silicone | 0.50 | 0.50 | 0.50 | 0.50 | — | — | 2.50 | 2.50 | 2.50 | 2.50 | 2.50 |
| (b): PPG400 | — | — | 5.00 | 5.00 | 2.50 | — | — | — | — | — | — |
| (b): Benzyloxyethanol | 1.00 | — | 1.00 | 1.00 | — | — | 1.50 | 1.50 | 1.50 | 1.50 | 3.00 |
| (b): Dipropylene glycol | 5.00 | — | — | — | 5.00 | — | 2.50 | 2.50 | 2.50 | 2.50 | 5.00 |
| (b): Phenoxyethanol | 0.10 | — | 0.10 | 0.10 | 0.10 | — | 0.10 | 0.10 | 0.10 | 0.10 | 0.10 |
| Phosphoric acid | q.s. | q.s. | q.s. | q.s. | q.s. | q.s. | q.s. | q.s. | q.s. | q.s. | q.s. |
| (a2): Lactic acid | 2.30 | — | 1.00 | 1.00 | 2.00 | — | 1.80 | — | 1.80 | 1.00 | 1.00 |
| (a2): Glycolic acid | — | — | 1.20 | 1.20 | — | — | — | — | — | — | — |
| (a1): Malic acid | — | — | — | — | — | — | — | 1.80 | — | — | — |
| Hydroxyethyl cellulose | 0.30 | 0.30 | 0.20 | 0.20 | — | — | 0.30 | 0.30 | 0.30 | 0.30 | 0.30 |
| Highly polymerized polyethylene glycol | — | — | 0.08 | 0.08 | 0.08 | 0.08 | — | — | — | — | — |
| 48 wt. % sodium hydroxide | q.s. | q.s. | q.s. | q.s. | q.s. | q.s. | q.s. | q.s. | q.s. | q.s. | q.s. |
| Perfume | 0.40 | 0.40 | 0.20 | 0.20 | 0.40 | 0.40 | 0.35 | 0.35 | 0.35 | 0.35 | 0.35 |
| Purified water | balance | balance | balance | balance | balance | balance | balance | balance | balance | balance | balance |
| pH (diluted to 20 times the weight with water, 25° C.) | 3.0 | 4.0 | 3.0 | 3.0 | 3.0 | 4.0 | 3.0 | 3.0 | 3.0 | 3.0 | 3.0 |

TABLE 5

|  | | Ex. 9 | Comp. Ex. 9 | Ex. 10 | Comp. Ex. 10 | Ex. 11 | Comp. Ex. 11 | Ex. 12 | Comp. Ex. 12 | Comp. Ex. 13 | Comp. Ex. 14 | Comp. Ex. 15 |
|---|---|---|---|---|---|---|---|---|---|---|---|---|
| Recovery (%) from signs formed by bending | Rightly after | 77 | 54 | 83 | 61 | 79 | 71 | 79 | 69 | 66 | 73 | 75 |
|  | One hour after | 96 | 81 | 97 | 87 | 97 | 92 | 97 | 90 | 89 | 94 | 94 |
| Feeling upon use (organoleptic evaluation) | | A | A | A | A | A | B | A | D | A | A | C |

Example 13

The following hair shampoo (pH 3.7) was prepared.

|  | (wt. %) |
|---|---|
| Sodium polyoxyethylene lauryl sulfate | 13.0 |
| Coconut oil monoethanolamide | 0.8 |
| Myristyl alcohol | 1.0 |
| Cationic cellulose | 0.4 |
| Lauric amidopropylbetaine | 2.5 |
| Pearl concentrate | 8.0 |
| Polypropylene glycol 400 | 1.0 |
| Benzyloxyethanol | 0.5 |
| Malic acid | 0.5 |
| Citric acid | 0.5 |
| Lactic acid | 0.7 |
| 48 wt. % Sodium hydroxide | q.s. |
| Perfume | 0.4 |
| Purified water | Balance |
|  | 100.0 |

Example 14

The following hair conditioner (pH 3.2) was prepared.

|  | (wt. %) |
|---|---|
| Stearylamidopropyldimethylamine · lactate | 3.5 |
| Stearyl alcohol | 6.0 |
| Dipentaerythritol fatty acid ester | 0.1 |
| Isopropyl palmitate | 0.5 |
| Methylpolysiloxane | 2.5 |
| Phenoxyethanol | 0.1 |
| Polypropylene glycol 400 | 2.0 |
| Benzyloxyethanol | 1.0 |
| Malic acid | 0.7 |
| Lactic cid | 1.0 |
| Glycolic acid | 1.0 |
| 48 wt. % Sodium hydroxide | q.s. |
| Perfume | 0.4 |
| Purified water | Balance |
|  | 100.0 |

Example 15

The following hair shampoo (A) and hair conditioner (B) were prepared as one hair cosmetic composition set.

| Hair shampoo (A) | (wt. %) |
|---|---|
| Sodium polyoxyethylene lauryl sulfate | 13.0 |
| Coconut oil monoethanolamide | 0.8 |
| Myristyl alcohol | 1.0 |
| Cationic cellulose | 0.4 |
| Lauric amidopropylbetaine | 2.5 |
| Pearl concentrate | 8.0 |
| Polypropylene glycol 400 | 1.0 |
| Benzyloxyethanol | 0.5 |
| Malic acid | 0.5 |
| Citric acid | 0.5 |
| Perfume | 0.4 |
| Purified water | Balance |
|  | 100.0 |

| Hair conditioner (B) | (wt. %) |
|---|---|
| Stearylamidopropyldimethylamine · lactate | 3.5 |
| Stearyl alcohol | 6.0 |
| Dipentaerythritol fatty acid ester | 0.1 |
| Isopropyl palmitate | 0.5 |
| Methylpolysiloxane | 2.5 |
| Phenoxyethanol | 0.1 |
| Polypropylene glycol 400 | 2.0 |
| Benzyloxyethanol | 1.0 |
| Lactic acid | 1.0 |
| Glycolic acid | 1.0 |
| Perfume | 0.4 |
| Purified water | Balance |
|  | 100.0 |

The invention claimed is:

1. A method of treating hair, comprising applying to the hair a hair cosmetic composition A and a hair cosmetic composition B in any order, wherein
    composition A is a first hair cosmetic composition comprising:
        (a) at least one polycarboxylic acid or a salt thereof wherein said polycarboxylic acid is selected from the group consisting of malonic acid, maleic acid and malic acid, and
        (c) at least one organic solvent selected from the group consisting of an aromatic alcohol, an alkylene carbonate and a polyol,
        at a weight ratio of (a)/(c)=0.6 or greater, and
    composition B is a second hair cosmetic composition comprising:
        (b) at least one hydroxymonocarboxylic acid or a salt thereof wherein said hydroxymonocarboxylic acid is selected from the group consisting of glycolic acid and lactic acid, and
        (c) at least one organic solvent selected from the group consisting of an aromatic alcohol, an alkylene carbonate and a polyol,
        at a weight ratio of (b)/(c)=0.25 or greater, and
    the pH at 25° C. of each of composition A and composition B is from 2 to 5.5 when diluted to 20 times by weight with water.

2. The method of treating hair of claim 1, wherein component (a) is malic acid or a salt thereof.

3. A cosmetic set comprising a first hair cosmetic composition A and a second hair cosmetic composition B, wherein the first hair cosmetic composition A comprises:
- (a) at least one polycarboxylic acid or a salt thereof wherein said polycarboxylic acid is selected from the group consisting of malonic acid, maleic acid and malic acid, and
- (c) at least one organic solvent selected from the group consisting of an aromatic alcohol, an alkylene carbonate and a polyol, at a weight ratio of (a)/(c)=0.6 or greater, and
the second hair cosmetic composition B comprises:
- (b) at least one hydroxymonocarboxylic acid or a salt thereof wherein said hydroxymonocarboxylic acid is selected from the group consisting of glycolic acid and lactic acid, and
- (c) at least one organic solvent selected from the group consisting of an aromatic alcohol, an alkylene carbonate and a polyol, at a weight ratio of (b)/(c)=0.25 or greater, and
the pH at 25° C. of each of composition A and composition B is from 2 to 5.5 when diluted to 20 times by weight with water.

4. The cosmetic set of claim 3, wherein component (a) is malic acid or a salt thereof.

5. The method according to claim 1, wherein (a) the at least one polycarboxylic acid is present in composition A in an amount of 0.1 to 20 wt %.

6. The method according to claim 1, wherein (b) the at least one hydroxymonocarboxylic acid is present in composition B in an amount of 0.1 to 20 wt %.

7. The method according to claim 1, wherein (c) the aromatic alcohol is selected from the group consisting of benzyl alcohol, cinnamyl alcohol, phenethyl alcohol, p-anisyl alcohol, p-methylbenzyl alcohol, phenoxyethanol and 2-benzyloxyethanol.

8. The method according to claim 1, wherein (c) the alkylene carbonate is selected from the group consisting of ethylene carbonate and propylene carbonate.

9. The method according to claim 1, wherein (c) the polyol is selected from the group consisting of ethylene glycol, glycerin, sorbitol, propylene glycol, 1,3-butylene glycol, dipropylene glycol, and polypropylene glycol.

10. The method according to claim 1, wherein (c) the at least one organic solvent is present in each of compositions A and B in an amount of 0.1 to 20 wt %.

11. The method according to claim 1, wherein the weight ratio of (a)/(c) is from 0.6 to 1.5.

12. The method according to claim 1, wherein the weight ratio of (b)/(c) is from 0.25 to 1.0.

13. The method according to claim 1, wherein the pH at 25° C. of each of compositions A and B is from 3 to 3.9 when diluted to 20 times by weight with water.

14. The method according to claim 1, wherein composition A is applied to the hair before composition B.

15. The cosmetic set of claim 3, further comprising at least one higher alcohol selected from the group consisting of cetyl alcohol, stearyl alcohol, aralkyl alcohol and behenyl alcohol.

16. The cosmetic set of claim 15, wherein the at least one higher alcohol is present in each of compositions A and B in an amount of 1 to 20 wt %.

* * * * *